US012740933B2

(12) United States Patent
Tanaka et al.

(10) Patent No.: US 12,740,933 B2
(45) Date of Patent: Sep. 22, 2026

(54) WATER-IN-OIL EMULSION COSMETIC

(71) Applicant: IWASE COSFA CO., LTD., Osaka (JP)

(72) Inventors: Ippei Tanaka, Osaka (JP); Kaisei Ryu, Osaka (JP); Keiko Iwasaki, Osaka (JP)

(73) Assignee: IWASE COSFA CO., LTD., Osaka (JP)

( * ) Notice: Subject to any disclaimer, the term of this patent is extended or adjusted under 35 U.S.C. 154(b) by 252 days.

(21) Appl. No.: 18/700,454

(22) PCT Filed: Oct. 11, 2022

(86) PCT No.: PCT/JP2022/037893
§ 371 (c)(1),
(2) Date: Apr. 11, 2024

(87) PCT Pub. No.: WO2023/063319
PCT Pub. Date: Apr. 20, 2023

(65) Prior Publication Data

US 2025/0017842 A1 Jan. 16, 2025

(30) Foreign Application Priority Data

Oct. 15, 2021 (JP) ................................ 2021-169526

(51) Int. Cl.
*A61K 8/73* (2006.01)
*A61Q 17/04* (2006.01)

(52) U.S. Cl.
CPC ................ *A61K 8/73* (2013.01); *A61Q 17/04* (2013.01); *A61K 2800/52* (2013.01); *A61K 2800/5922* (2013.01); *A61K 2800/651* (2013.01)

(58) Field of Classification Search
CPC ........................................................ A61K 8/73
See application file for complete search history.

(56) References Cited

U.S. PATENT DOCUMENTS 5,840,883 A 11/1998 Suzuki et al.

FOREIGN PATENT DOCUMENTS

| | | | |
|---|---|---|---|
| JP | 8-277302 | 10/1996 | |
| JP | 11-21224 | 1/1999 | |
| JP | 2001-187711 | 7/2001 | |
| JP | 2008-179628 | 8/2008 | |
| JP | 2021-80229 | 5/2021 | |
| JP | 2021-88532 | 6/2021 | |
| WO | WO-2017141919 A1 * | 8/2017 | ............ A61Q 17/04 |
| WO | 2021/200781 | 10/2021 | |

OTHER PUBLICATIONS

International Search Report issued Dec. 20, 2022 in International (PCT) Application No. PCT/JP2022/037893.
International Preliminary Report on Patentability issued Apr. 16, 2024 in International (PCT) Application No. PCT/JP2022/037893.

* cited by examiner

*Primary Examiner* — Benjamin J Packard
(74) *Attorney, Agent, or Firm* — Wenderoth, Lind & Ponack, L.L.P.

(57) ABSTRACT

Provide is a water-in-oil emulsion cosmetic having improved ultraviolet-protective effect, excellent smoothness and non-powdery finish, and excellent dispersibility and emulsion stability. The water-in-oil emulsion cosmetic includes a first polysaccharide fatty acid ester containing dextrin isostearate; a second polysaccharide fatty acid ester containing at least one selected from the group consisting of dextrin fatty acid esters, inulin fatty acid esters, and sucrose fatty acid esters, other than dextrin isostearate; metal oxide particles having an average primary particle size of not more than 200 nm; and water. The content ratio of the first polysaccharide fatty acid ester is 0.1% by mass to 4% by mass and the content ratio of the second polysaccharide fatty acid ester is 0.1% by mass to 2% by mass.

8 Claims, No Drawings

WATER-IN-OIL EMULSION COSMETIC

TECHNICAL FIELD

The present invention relates to a water-in-oil emulsion cosmetic.

BACKGROUND ART

As a technique related to cosmetics, JP H08-277302 A describes a cosmetic including a dextrin fatty acid ester. JP H11-021224 A describes an ultraviolet-protective composition including a dextrin fatty acid ester. JP 2001-187711 A describes stability of a water-in-oil emulsion including a dextrin fatty acid ester. JP 2008-179628 A describes a low-viscosity water-in-oil emulsion sunscreen having excellent stability over time. JP 2021-80229 A describes an oil-based solid cosmetic including a polysaccharide fatty acid ester and metal oxide particles.

SUMMARY OF THE INVENTION

Problems to be Solved by the Invention

An object of one aspect of the present invention is to provide a water-in-oil emulsion cosmetic having improved ultraviolet-protective effect, excellent smoothness and non-powdery finish, and excellent dispersibility and emulsion stability.

Means for Solving the Problems

The following are specific means to solve the above problem, and the present invention includes the following aspects. A first aspect is a water-in-oil emulsion cosmetic including:

- a first polysaccharide fatty acid ester containing dextrin isostearate;
- a second polysaccharide fatty acid ester containing at least one selected from the group consisting of dextrin fatty acid esters, inulin fatty acid esters, and sucrose fatty acid esters, other than dextrin isostearate;
- metal oxide particles having an average primary particle size of not more than 200 nm; and
- water.

In the water-in-oil emulsion cosmetic, the content ratio of the first polysaccharide fatty acid ester is 0.1% by mass to 4% by mass, and the content ratio of the second polysaccharide fatty acid ester is 0.1% by mass to 2% by mass.

In one mode, the water content ratio may be 10% by mass to 60% by mass. In one mode, the content ratio of the metal oxide particles may be 6% by mass to 40% by mass. In one mode, the second polysaccharide fatty acid ester may contain at least one selected from the group consisting of dextrin palmitate, dextrin (palmitate/ethylhexanoate), dextrin (palmitate/hexyldecanoate), inulin stearate, and dextrin myristate. In one mode, the total content ratio of the first polysaccharide fatty acid ester and the second polysaccharide fatty acid ester may be 0.2% by mass to 6% by mass, and the mass ratio of the content of the second polysaccharide fatty acid ester to the content of the first polysaccharide fatty acid ester may be 0.05 to 8. In one mode, the ratio of the content of the first polysaccharide fatty acid ester to the content of the metal oxide particles may be 0.003 to 0.16; the ratio of the content of the second polysaccharide fatty acid ester to the content of the metal oxide particles may be 0.003 to 0.08; and the ratio of the total content of the first polysaccharide fatty acid ester and the second polysaccharide fatty acid ester to the total content of the metal oxide particles may be 0.006 to 0.25. In one mode, the metal oxide particles may have an average particle size of 5 nm to 200 nm.

Effect of the Invention

According to one aspect of the present invention, a water-in-oil emulsion cosmetic having improved ultraviolet-protective effect, excellent smoothness and non-powdery finish, and excellent dispersibility and emulsion stability, may be provided.

MODE FOR CARRYING OUT THE INVENTION

The term "step" as used herein encompasses not only an independent step but also a step not clearly distinguishable from another step as long as the intended purpose of the step is achieved. If multiple substances correspond to a component in a composition, the content of the component in the composition means the total amount of the multiple substances present in the composition unless otherwise specified. Further, upper limit and lower limit values that are described for a numerical range in the present specification can be arbitrarily selected and combined. Embodiments of the present invention will now be described in detail. The embodiments described below are exemplifications of a water-in-oil emulsion cosmetic for embodying the technical ideas of the present invention, and the present invention is not limited to the water-in-oil emulsion cosmetic described below.

Water-In-Oil Emulsion Cosmetic

A water-in-oil emulsion cosmetic includes: a first polysaccharide fatty acid ester containing dextrin isostearate; a second polysaccharide fatty acid ester other than dextrin isostearate; and metal oxide particles. The water-in-oil emulsion cosmetic may be, for example, an ultraviolet-protective cosmetic.

Since the water-in-oil emulsion cosmetic includes not only dextrin isostearate, but also a polysaccharide fatty acid ester other than dextrin isostearate, the ultraviolet-protective effect due to the metal oxide particles can be synergistically improved. Further, since the water-in-oil emulsion cosmetic includes at least two polysaccharide fatty acid esters including dextrin isostearate, smoother feeling of use can be obtained; powdery finish can be effectively suppressed; and the dispersibility and the emulsion stability can be improved. This is thought to be due to, for example, the following reasons. The first polysaccharide fatty acid ester has a pigment dispersibility to enable formation of a uniform film. Combined use of the first polysaccharide fatty acid ester with the second polysaccharide fatty acid ester, which has a very high pigment dispersibility, is thought to enable formation of a more uniform UV-protective film, resulting in a synergistically increased SPF value.

Ultraviolet-protective cosmetics often contain metal oxide particles having ultraviolet-protective effect. In general, such metal oxide particles tend to aggregate in a formulation, and hence often fail to produce an expected ultraviolet-protective effect, or result in unfavorable usability that leads to powdery finish or the like, which is problematic. However, inclusion of a large amount of a dispersant for the purpose of suppressing the aggregation causes, as another problem, poor feeling of use such as stickiness and the lack of smoothness. The water-in-oil emulsion cosmetic of the present invention includes not only dextrin isostearate, but also a polysaccharide fatty acid ester other than dextrin isostearate. Therefore, an ultraviolet-protective cosmetic with an improved ultraviolet-protective effect of the metal oxide particles, excellent feeling of use regarding smoothness and non-powdery finish, and excellent dispersibility and emulsion stability, can be obtained.

The water-in-oil emulsion cosmetic includes at least two polysaccharide fatty acid esters: the first polysaccharide fatty acid ester and the second polysaccharide fatty acid ester. The polysaccharide fatty acid esters may be oil-phase thickeners that constitute an ultraviolet-protective cosmetic. The first polysaccharide fatty acid ester contains dextrin isostearate. The dextrin isostearate is not limited as long as it is an ester of dextrin or reduced dextrin and isostearic acid, and as long as it is commonly used for cosmetics. The average degree of polymerization of sugars of the dextrin or reduced dextrin may be, for example, 3 to 150. The isostearic acid herein means one type of branched stearic acid, or a mixture of two or more types of branched stearic acid. The first polysaccharide fatty acid ester may be substantially composed of dextrin isostearate. The term "substantially" herein means that the amount of other components inevitably contained is not more than 5% by mass or not more than 1% by mass.

In the water-in-oil emulsion cosmetic, the content ratio of the first polysaccharide fatty acid ester may be, for example, 0.1% by mass to 4% by mass. The content ratio of the first polysaccharide fatty acid ester may be preferably not less than 0.3% by mass, not less than 0.5% by mass, not less than 0.7% by mass, or not less than 1% by mass, and may be preferably not more than 3% by mass or not more than 2% by mass.

In the water-in-oil emulsion cosmetic, the ratio of the content of the first polysaccharide fatty acid ester to the content of the metal oxide particles may be, for example, 0.003 to 0.16, or 0.004 to 0.154. The ratio of the content of the first polysaccharide fatty acid ester to the content of the metal oxide particles may be preferably not less than 0.008 or not less than 0.011, and may be preferably not more than 0.1, not more than 0.08, or not more than 0.076.

The second polysaccharide fatty acid ester is not limited as long as it is not dextrin isostearate. Examples of the second polysaccharide fatty acid ester may include a dextrin fatty acid ester, an inulin fatty acid ester, and a sucrose fatty acid ester. The second polysaccharide fatty acid ester may contain at least one selected from the group consisting of these.

The dextrin fatty acid ester is not limited as long as it is an ester of dextrin or reduced dextrin and a higher fatty acid, and as long as it is commonly used for cosmetics. The average degree of polymerization of sugars of the dextrin or reduced dextrin may be, for example, 3 to 150. The fatty acid constituting the dextrin fatty acid ester may be, for example, a $C_8$-$C_{22}$ saturated fatty acid. Specific examples of the dextrin fatty acid ester include dextrin palmitate, dextrin (palmitate/2-ethylhexanoate), dextrin (palmitate/hexyldecanoate), dextrin myristate, dextrin oleate, and dextrin stearate.

The inulin fatty acid ester is not limited as long as it is an ester of inulin and a higher fatty acid, and as long as it is commonly used for cosmetics. The average degree of polymerization of sugars of the inulin may be, for example, 3 to 150. The fatty acid constituting the inulin fatty acid ester may be, for example, a $C_8$-$C_{22}$ saturated fatty acid. Specific examples of the inulin fatty acid ester include inulin palmitate, inulin myristate, inulin oleate, and inulin stearate.

The sucrose fatty acid ester is not limited as long as it is an ester of sucrose and a higher fatty acid, and as long as it is commonly used for cosmetics. The fatty acid constituting the sucrose fatty acid ester may be either linear or branched, and may be either saturated or unsaturated. $C_{12}$-$C_{22}$ fatty acids may be preferably used. Specific examples of the sucrose fatty acid ester include sucrose caprylate, sucrose caprate, sucrose laurate, sucrose myristate, sucrose palmitate, sucrose stearate, sucrose oleate, and sucrose erucate.

The second polysaccharide fatty acid ester preferably contains at least one selected from the group consisting of dextrin fatty acid esters and inulin fatty acid esters, preferably contains at least one selected from the group consisting of dextrin palmitate, dextrin (palmitate/ethylhexanoate), dextrin (palmitate/hexyldecanoate), inulin stearate, and dextrin myristate. A single type of second polysaccharide fatty acid ester may be used, or two or more types of second polysaccharide fatty acid esters may be used in combination.

In the water-in-oil emulsion cosmetic, the content ratio of the second polysaccharide fatty acid ester may be, for example, 0.1% by mass to 2% by mass. The content ratio of the second polysaccharide fatty acid ester may be preferably not less than 0.3% by mass or not less than 0.5% by mass, and may be preferably not more than 1.5% by mass.

In the water-in-oil emulsion cosmetic, the total content ratio of the first polysaccharide fatty acid ester and the second polysaccharide fatty acid ester may be, for example, 0.2% by mass to 6% by mass. The total content ratio of the first and second polysaccharide fatty acid esters may be preferably not less than 0.5% by mass, not less than 1% by mass, not less than 1.2% by mass, or not less than 1.5% by mass, and may be preferably not more than 4% by mass, not more than 3.5% by mass, or not more than 3% by mass. However, the content ratio of the first polysaccharide fatty acid ester does not exceed 4% by mass, and the content ratio of the second polysaccharide fatty acid ester does not exceed 2% by mass.

In the water-in-oil emulsion cosmetic, the ratio of the content of the second polysaccharide fatty acid ester to the content of the first polysaccharide fatty acid ester may be, for example, 0.05 to 8, or 0.1 to 8. The ratio of the content of the second polysaccharide fatty acid ester to the content of the first polysaccharide fatty acid ester may be preferably not less than 0.2 or not less than 0.3, and may be preferably not more than 7, not more than 6.7, not more than 5, or not more than 3.

In the water-in-oil emulsion cosmetic, the ratio of the content of the second polysaccharide fatty acid ester to the content of the metal oxide particles may be, for example, 0.003 to 0.08, or 0.003 to 0.06. The ratio of the content of the second polysaccharide fatty acid ester to the content of the metal oxide particles may be preferably not less than 0.01, not less than 0.013, or not less than 0.018, and may be preferably not more than 0.053 or not more than 0.04.

The water-in-oil emulsion cosmetic includes at least one of metal oxide particles having an average primary particle size of not more than 200 nm. The metal oxide particles may be an ultraviolet-protective agent constituting a water-in-oil emulsion cosmetic, and may be an ultraviolet-scattering agent. From the viewpoint of the ultraviolet-scattering effect, the metal oxide particles may have an average primary particle size of, for example, 5 nm to 200 nm, preferably not less than 10 nm or not less than 15 nm, and preferably not more than 150 nm, not more than 100 nm, or not more than 80 nm. The average primary particle size of the metal oxide particles may be, but does not necessarily need to be, measured by a method commonly used. The average primary particle size of the metal oxide particles may be, for example, the average of the primary particle sizes of primary particles whose outlines can be identified from a transmission electron microscope (TEM) image, wherein each primary particle size is calculated as the arithmetic average of the long-axis length and the short-axis length. The average primary particle size of the metal oxide particles may also be a value described in available specifications of the metal oxide particles, a nominal value provided by the manufacturer, or the like. The metal oxide particles may have any shape, including spherical shapes, plate-like shapes, rod-like shapes, spindle-like shapes, needle-like shapes, and amorphous shapes.

In cases where the average primary particle size of the metal oxide particles is within the range described above, high visible light transparency and a favorable ultraviolet-blocking range can be achieved, which is preferred. Further, in cases where the particle size is not more than 200 nm, a decrease in the visible light transparency and a decrease in the ultraviolet-blocking performance tend to be suppressed. Further, in cases where the particle size is not less than 5 nm, a decrease in the ultraviolet-blocking performance tends to be more suppressed.

Specific examples of the metal oxide constituting the metal oxide particles include zinc oxide, titanium oxide, aluminum oxide, iron oxide, cerium oxide, tungsten oxide, zirconium oxide, and chromium oxide. The metal oxide particles may contain at least one selected from the group consisting of these. The metal oxide particles may preferably contain at least one selected from the group consisting of zinc oxide, titanium oxide, aluminum oxide, and iron oxide. A single type of metal oxide particles may be used, or two or more types of metal oxide particles may be used in combination. In cases where two or more types of metal oxide particles are used, for example, zinc oxide and titanium oxide may be used in combination; titanium oxide and aluminum oxide may be used in combination; or titanium oxide, aluminum oxide, and zinc oxide may be used in combination.

In cases where two or more types of metal oxide particles are used, metal oxide particles having different average primary particle sizes may be used in combination. For example, in cases where two types of metal oxide particles having different average primary particle sizes are used, one type of metal oxide particles may have an average primary particle size of, for example, 5 nm to 200 nm, preferably not less than 10 nm or not less than 20 nm, and preferably not more than 150 nm, not more than 100 nm, or not more than 80 nm. The other type of metal oxide particles may have an average primary particle size of, for example, 5 nm to 200 nm, preferably not less than 10 nm, and preferably not more than 150 nm, not more than 80 nm, or not more than 50 nm. The ratio of the average primary particle size of one type of metal oxide particles to the average primary particle size of the other type of metal oxide particles may be, for example, 0.2 to 1.2, preferably not less than 0.3 or not more than 1.

The metal oxide particles may have an untreated surface, or may have a surface subjected to a certain type of hydrophobization. The metal oxide particles preferably have a hydrophobized surface. Examples of a hydrophobizing surface treatment agent that may be used include those commonly used in the field of cosmetics, including silicones such as dimethicone, hydrogen dimethicone, and alkyl-modified silicones; alkoxysilanes such as octyltriethoxysilane; dextrin fatty acid esters such as dextrin palmitate; and fatty acids such as stearic acid. The surface treatment agent for the metal oxide particles may be an inorganic substance such as aluminum hydroxide or silica.

In the water-in-oil emulsion cosmetic, the content ratio of the metal oxide particles may be, for example, 6% by mass to 40% by mass. The content ratio of the metal oxide particles may be preferably not less than 7% by mass, not less than 8% by mass, not less than 9% by mass, not less than 15% by mass, or not less than 20% by mass, and may be preferably not more than 35% by mass or not more than 30% by mass.

In the water-in-oil emulsion cosmetic, the ratio of the total content of the first polysaccharide fatty acid ester and the second polysaccharide fatty acid ester to the total content of the metal oxide particles may be, for example, 0.006 to 0.25, or 0.008 to 0.25. The ratio of the total content of the first polysaccharide fatty acid ester and the second polysaccharide fatty acid ester to the total content of the metal oxide particles may be preferably not less than 0.03, not less than 0.039, or not less than 0.05, and may be preferably not more than 0.232, not more than 0.16, or not more than 0.116.

In the water-in-oil emulsion cosmetic, the content ratio of water may be, for example, 10% by mass to 60% by mass. The content ratio of water may be preferably not less than 15% by mass or not less than 20% by mass, and may be preferably not more than 50% by mass or not more than 40% by mass.

The water-in-oil emulsion cosmetic may include an ultraviolet absorber as an ultraviolet-protective agent. Examples of the ultraviolet absorber include organic ultraviolet absorbers such as ethylhexyl methoxycinnamate, octocrylene, polysilicone-15, t-butylmethoxydibenzoylmethane, ethylhexyl triazone, hexyl diethylaminohydroxybenzoylbenzoate, bis-ethylhexyloxyphenol methoxyphenyl triazine, oxybenzone-3, methylene bis-benzotriazolyl tetramethylbutylphenol, phenylbenzimidazole sulfonic acid, homosalate, and ethylhexyl salicylate.

In addition to the first polysaccharide fatty acid ester, the second polysaccharide fatty acid ester, and the metal oxide particles, the water-in-oil emulsion cosmetic may include other optional components that may be usually included in water-in-oil emulsion cosmetics. Examples of the other optional components include, but are not limited to, liquid oils; water-soluble polymers; oil-soluble polymers; solid oils such as waxes; lower alcohols; moisturizing components; surfactants; powder components; antiseptic components; and drugs.

Examples of the liquid oils include silicone oils, hydrocarbon oils, vegetable oils, ester oils, and high-molecular-weight polyoxyalkylene glycols. Specific examples of the liquid oils include silicone oils such as dimethicone, diphenyl dimethicone, and cyclopentasiloxane; liquid oils and fats such as linseed oil, camellia oil, macadamia nut oil, corn oil, olive oil, avocado oil, sasanqua oil, castor oil, safflower oil, apricot kernel oil, cinnamon oil, jojoba oil, grape seed oil, almond oil, rapeseed oil, sesame oil, sunflower oil, wheat germ oil, rice germ oil, rice bran oil, cottonseed oil, soybean oil, peanut oil, tea seed oil, evening primrose oil, egg-yolk oil, cod-liver oil, triglycerin, glyceryl trioctanoate, and glyceryl triisopalmitate; ester oils which includes octanoates such as cetyl octanoate, isooctanoates such as glyceryl tri-2-ethylhexanoate and pentaerythritol tetra-2-ethylhexanoate, laurates such as hexyl laurate, myristates such as isopropyl myristate and octyldodecyl myristate, palmitates such as octyl palmitate, stearates such as isocetyl stearate; isostearates such as isopropyl isostearate, isopalmitates such as octyl isopalmitate, oleates such as isodecyl oleate, adipic acid diesters such as diisopropyl adipate, sebacic acid diesters such as diethyl sebacate, and diisostearyl malate; hydrocarbon oils such as liquid paraffin and squalane; and polyoxybutylene polyoxypropylene glycol.

Examples of the water-soluble polymers include homopolymers and copolymers of 2-acrylamide-2-methylpropanesulfonic acid (hereinafter simply referred to as "AMPS"). The copolymers contain comonomers such as vinylpyrrolidone, acrylic acid amide, sodium acrylate, or hydroxyethyl acrylate. Thus, examples of the water-soluble polymers include AMPS homopolymers, vinylpyrrolidone/AMPS copolymers, dimethylacrylamide/AMPS copolymers, acrylic acid amide/AMPS copolymers, and sodium acrylate/AMPS copolymers. Examples of the water-soluble polymers also include carboxyvinyl polymers, ammonium polyacrylate, sodium polyacrylate, sodium acrylate/alkyl acrylate/sodium methacrylate/alkyl methacrylate copolymers, carrageenan, pectin, mannan, curdlan, chondroitin sulfate, starch, glycogen, gum arabic, sodium hyaluronate, tragacanth gum, xanthan gum, mucoitin sulfate, hydroxyethyl guar gum, carboxymethyl guar gum, guar gum, dextran, keratosulfate, locust bean gum, succinoglucan, chitin, chitosan, carboxymethyl chitin, and agar.

Examples of the oil-soluble polymers include trimethylsiloxysilicate, alkyl-modified silicone, polyamide-modified silicone, dimethicone crosspolymers, (dimethicone/vinyl dimethicone) crosspolymers, and polymethylsilsesquioxane.

Examples of the waxes include beeswax, candelilla wax, carnauba wax, lanolin, liquid lanolin, and jojoba wax.

Examples of the lower alcohols include $C_1$-$C_5$ alcohols such as ethanol and isopropanol. Examples of the moisturizing components include polyalcohols such as ethylene glycol, propylene glycol, 1,3-butylene glycol, dipropylene glycol, and polybutylene glycol.

Examples of the surfactants include anionic, cationic, nonionic, and zwitterionic surfactants, and include silicone surfactants and hydrocarbon surfactants. Examples of the powder components include nylon or acrylic polymer spherical powders, silica powders, and silicone powders.

Examples of the drugs include salts of L-ascorbic acid and derivatives thereof; glycyrrhizinates and derivatives thereof such as dipotassium glycyrrhizinate and monoammonium glycyrrhizinate; glycyrrhetinates and derivatives thereof such as stearyl glycyrrhetinate; allantoin; salts of tranexamic acid and derivatives thereof; salts of alkoxysalicylic acid and derivatives thereof; salts of glutathione and derivatives thereof; allantoin; and azulene.

Examples of other components include sugars such as trehalose and erythritol; polysaccharides such as hyaluronic acid and acetylated hyaluronic acid; amino acids such as serine, glycine, hydroxyproline, glutamic acid, and alanine; and extracts such as silk extract, chlorella extract, hydrolyzed pearl protein, yaguruma (cornflower) extract, tencha (*Rubus suavissimus*) extract, yeast extract, inositol, licorice extract, burnet extract, rose extract, and coix seed.

Specific examples of the dosage form of the water-in-oil emulsion cosmetic include sunscreen emulsions and sunscreen creams. These may be produced by an ordinary method suitable for each dosage form.

The present invention encompasses, as another aspect, a water-in-oil emulsion cosmetic for use in ultraviolet protection, the water-in-oil emulsion cosmetic including: the first polysaccharide fatty acid ester; the second polysaccharide fatty acid ester; the metal oxide particles having an average primary particle size of not more than 200 nm; and water.

EXAMPLES

The present invention is described below more concretely by way of Examples. However, the present invention is not limited to these Examples.

Examples 1 to 14, and Comparative Examples 1 to 9

Components with the display names listed in Table 1 were uniformly mixed together to achieve the content ratios (% by mass) listed in Table 1, to produce sunscreen agents as ultraviolet-protective cosmetics.

Examples 15 to 19, and Comparative Examples 10 to 16

Components with the display names listed in Table 2 were uniformly mixed together to achieve the content ratios (% by mass) listed in Table 2, to produce sunscreen agents as ultraviolet-protective cosmetics.

Examples 20 to 23, and Comparative Example 17

Components with the display names listed in Table 3 were uniformly mixed together to achieve the content ratios (% by mass) listed in Table 3, to produce sunscreen agents as ultraviolet-protective cosmetics.

The obtained sunscreen agents were used to perform an evaluation on "ultraviolet-protective effect (SPF-increasing effect)", "usability (smoothness)", "non-powdery finish", and "stability of the preparation" as follows, and the overall rating was carried out based on the evaluation results. The results are shown in Table 1 and Table 2. Details of the components in Table 1 and Table 2 are described later.

Evaluation Methods

1. Ultraviolet-Protective Effect (SPF-Increasing Effect)

For the evaluation of the SPF-increasing effect, each sunscreen agent obtained as described above as a W/O emulsion cosmetic was applied to PMMA (manufactured by Labsphere; HELIOPLATE HD 6) at 1.3 mg/cm$^2$, and left to stand for 15 minutes to provide a sample. The SPF value of the sample was measured using an SPF analyzer (manufactured by Labsphere; UV-2000 S). Based on the obtained SPF value, the SPF-increasing rate was calculated using the following calculation equation, and a rating on a 5-point scale was carried out based on the following criteria.

Calculation equation:

SPF-increasing rate=(SPF value/(SPF value in Comparative Example 1)−1)×100(%)

Criteria

4 Points: The SPF-increasing rate was more than 60%.

3 Points: The SPF-increasing rate was more than 40% and not more than 60%.

2 Points: The SPF-increasing rate was more than 20% and not more than 40%.

1 Point: The SPF-increasing rate was more than 0% and not more than 20%.

0 Points: The SPF-increasing rate was 0%.

2. Evaluation of Smoothness and Non-Powdery Finish

Each sunscreen agent obtained as described above was evaluated on the smoothness and the non-powdery finish by sensory evaluation. In the sensory evaluation, a rating on a 5-point scale was carried out by 12 panelists who specialize in the evaluation of cosmetics, based on the following criteria. It should be noted that a preliminary test was carried out by the panelists who specialize in evaluation of cosmetics, to confirm that the rating was almost consistent among the panelists.

Criteria

4 Points: Excellent
3 Points: Good
2 Points: Fair
1 Point: Poor
0 Points: Very poor 3. Stability of Formulation Each sunscreen agent obtained as described above was stored in a thermostat at 50° C. for 1 week. The sample after the storage was subjected to evaluation of the external appearance by visual observation, and to evaluation of the uniformity of emulsified droplets under the microscope. In the evaluation of the external appearance by visual observation, a rating on a 4-point scale was carried out based on the following criteria A. In the evaluation of the uniformity of emulsified droplets under the microscope, a rating on a 4-point scale was carried out based on the following criteria B. Further, based on the resulting scores, stability of each preparation was rated according to the following criteria C.

Criteria A [Evaluation of the External Appearance by Visual Observation]

4 Points: No creaming was found at all (excellent).
3 Points: Slight oil flotation was found (rather good).
2 Points: Oil flotation was found (rather poor).
1 Point: Separation occurred (poor).

Criteria B [Evaluation of the Uniformity of Emulsified Droplets Under the Microscope]

4 Points: Very uniform (excellent).
3 Points: Uniform (rather good).
2 Points: Rather nonuniform (rather poor).
1 Point: Nonuniform (poor).

Criteria C [Stability of the Preparation]

4 Points: The sum of the scores according to criteria A and criteria B was 8 (excellent).
3 Points: The sum of the scores according to criteria A and criteria B was 6 or not less than 7 (rather good).
2 Points: The sum of the scores according to criteria A and criteria B was 4 or 5 (rather poor).
1 Point: The sum of the scores according to criteria A and criteria B was 3 or less (poor).

5. Overall Rating

The overall rating was carried out based on the sum of the scores on the SPF-increasing effect, the smoothness, the non-powdery finish, and the stability of the preparation.

TABLE 1

| Display name | Dextrin palmitate | Dextrin isostearate | Squalane | Neopenty Iglycol dicaprate | Lauryl PEG-9 polydimethylsiloxyethyl dimethicone | Diphenylsiloxyphenyl trimethicone | Cyclopentasiloxane | Titanium oxide, Al hydroxide, stearic acid #1 |
|---|---|---|---|---|---|---|---|---|
| Example1 | 0.3 | 0.3 | 3.0 | 3.0 | 3.0 | 1.5 | 35.4 | 8.5 |
| Example2 | 0.3 | 4.0 | 3.0 | 3.0 | 3.0 | 1.5 | 31.7 | 8.5 |
| Example3 | 0.5 | 0.5 | 3.0 | 3.0 | 3.0 | 1.5 | 35.0 | 8.5 |
| Example4 | 0.5 | 1.0 | 3.0 | 3.0 | 3.0 | 1.5 | 34.5 | 8.5 |
| Example5 | 0.5 | 1.5 | 3.0 | 3.0 | 3.0 | 1.5 | 34.0 | 8.5 |
| Example6 | 0.5 | 2.0 | 3.0 | 3.0 | 3.0 | 1.5 | 33.5 | 8.5 |
| Example7 | 1.0 | 0.5 | 3.0 | 3.0 | 3.0 | 1.5 | 34.5 | 8.5 |
| Example8 | 1.0 | 1.0 | 3.0 | 3.0 | 3.0 | 1.5 | 34.0 | 8.5 |
| Example9 | 1.0 | 2.0 | 3.0 | 3.0 | 3.0 | 1.5 | 33.0 | 8.5 |
| Example10 | 2.0 | 0.3 | 3.0 | 3.0 | 3.0 | 1.5 | 33.7 | 8.5 |
| Example11 | 2.0 | 0.5 | 3.0 | 3.0 | 3.0 | 1.5 | 33.5 | 8.5 |
| Example12 | 2.0 | 4.0 | 3.0 | 3.0 | 3.0 | 1.5 | 30.0 | 8.5 |
| Example13 | 0.1 | 0.1 | 3.0 | 3.0 | 3.0 | 1.5 | 35.8 | 8.5 |
| Example14 | 0.2 | 0.2 | 3.0 | 3.0 | 3.0 | 1.5 | 35.6 | 8.5 |
| Comparative Example 1 | — | — | 3.0 | 3.0 | 3.0 | 1.5 | 36.0 | 8.5 |
| Comparative Example 2 | 0.5 | — | 3.0 | 3.0 | 3.0 | 1.5 | 34.5 | 8.5 |
| Comparative Example 3 | — | 0.5 | 3.0 | 3.0 | 3.0 | 1.5 | 35.5 | 8.5 |
| Comparative Example 4 | 2.0 | — | 3.0 | 3.0 | 3.0 | 1.5 | 34.0 | 8.5 |
| Comparative Example 5 | — | 4.0 | 3.0 | 3.0 | 3.0 | 1.5 | 32.0 | 8.5 |
| Comparative Example 6 | 5.5 | 0.5 | 3.0 | 3.0 | 3.0 | 1.5 | 34.0 | 8.5 |
| Comparative Example 7 | 0.3 | 5.7 | 3.0 | 3.0 | 3.0 | 1.5 | 32.0 | 8.5 |
| Comparative Example 8 | 3.0 | 3.0 | 3.0 | 3.0 | 3.0 | 1.5 | 32.0 | 8.5 |
| Comparative Example 9 | 2.5 | 0.5 | 3.0 | 3.0 | 3.0 | 1.5 | 32.0 | 8.5 |

| Display name | Zinc oxide, hydrogen dimethicone #5 | Water | Propane diol | NaCl | Phenoxy ethanol | SPF-Increasing Effect | Usability (Smooth ness) | Non-Powdery Finish | Stability of Formulation | Overall Rating |
|---|---|---|---|---|---|---|---|---|---|---|
| Example1 | 17.4 | 20.3 | 6.0 | 1.0 | 0.3 | 2 | 4 | 4 | 3 | 13 |
| Example2 | 17.4 | 20.3 | 6.0 | 1.0 | 0.3 | 4 | 2 | 4 | 4 | 14 |

TABLE 1-continued

| | | | | | | | | | | |
|---|---|---|---|---|---|---|---|---|---|---|
| Example3 | 17.4 | 20.3 | 6.0 | 1.0 | 0.3 | 3 | 4 | 4 | 4 | 15 |
| Example4 | 17.4 | 20.3 | 6.0 | 1.0 | 0.3 | 4 | 4 | 4 | 4 | 16 |
| Example5 | 17.4 | 20.3 | 6.0 | 1.0 | 0.3 | 4 | 4 | 4 | 4 | 16 |
| Example6 | 17.4 | 20.3 | 6.0 | 1.0 | 0.3 | 4 | 4 | 4 | 4 | 16 |
| Example7 | 17.4 | 20.3 | 6.0 | 1.0 | 0.3 | 4 | 4 | 4 | 4 | 16 |
| Example8 | 17.4 | 20.3 | 6.0 | 1.0 | 0.3 | 4 | 4 | 4 | 4 | 16 |
| Example9 | 17.4 | 20.3 | 6.0 | 1.0 | 0.3 | 4 | 4 | 4 | 4 | 16 |
| Example10 | 17.4 | 20.3 | 6.0 | 1.0 | 0.3 | 4 | 3 | 4 | 4 | 15 |
| Example11 | 17.4 | 20.3 | 6.0 | 1.0 | 0.3 | 4 | 3 | 4 | 4 | 15 |
| Example12 | 17.4 | 20.3 | 6.0 | 1.0 | 0.3 | 4 | 2 | 2 | 4 | 12 |
| Example13 | 17.4 | 20.3 | 6.0 | 1.0 | 0.3 | 2 | 3 | 4 | 3 | 12 |
| Example14 | 17.4 | 20.3 | 6.0 | 1.0 | 0.3 | 2 | 3 | 4 | 3 | 12 |
| Comparative Example 1 | 17.4 | 20.3 | 6.0 | 1.0 | 0.3 | 0 | 1 | 1 | 1 | 3 |
| Comparative Example 2 | 17.4 | 20.3 | 6.0 | 1.0 | 0.3 | 1 | 2 | 1 | 3 | 7 |
| Comparative Example 3 | 17.4 | 20.3 | 6.0 | 1.0 | 0.3 | 1 | 3 | 4 | 1 | 9 |
| Comparative Example 4 | 17.4 | 20.3 | 6.0 | 1.0 | 0.3 | 4 | 1 | 1 | 4 | 10 |
| Comparative Example 5 | 17.4 | 20.3 | 6.0 | 1.0 | 0.3 | 3 | 2 | 4 | 1 | 10 |
| Comparative Example 6 | 17.4 | 20.3 | 6.0 | 1.0 | 0.3 | 4 | 0 | 0 | 4 | 8 |
| Comparative Example 7 | 17.4 | 20.3 | 6.0 | 1.0 | 0.3 | 4 | 0 | 0 | 1 | 5 |
| Comparative Example 8 | 17.4 | 20.3 | 6.0 | 1.0 | 0.3 | 4 | 0 | 0 | 4 | 8 |
| Comparative Example 9 | 17.4 | 20.3 | 6.0 | 1.0 | 0.3 | 4 | 0 | 0 | 4 | 8 |

TABLE 2

| Display name | Example15 | Example16 | Example17 | Example18 | Example19 | Example10 Comparative | Example11 Comparative |
|---|---|---|---|---|---|---|---|
| Dextrin palmitate | 0.5 | — | — | — | — | — | 0.5 |
| Dextrin (palmitate/ethylhexanoate) | — | 0.5 | — | — | — | — | — |
| Inulin stearate | — | — | 0.5 | — | — | — | — |
| Dextrin myristate | — | — | — | 0.5 | — | — | — |
| Dextrin (palmitate/hexyldecanoate) | — | — | — | — | 0.5 | — | — |
| Dextrin isostearate | 1.0 | 1.0 | 1.0 | 1.0 | 1.0 | — | — |
| Squatane | 3.0 | 3.0 | 3.0 | 3.0 | 3.0 | 3.0 | 3.0 |
| Neopentylglycol dicaprate | 3.0 | 3.0 | 3.0 | 3.0 | 3.0 | 3.0 | 3.0 |
| Lauryl PEG-9 polydimethylsiloxyethyl dimethicone | 3.0 | 3.0 | 3.0 | 3.0 | 3.0 | 3.0 | 3.0 |
| Diphenylsiloxyphenyl trimethicone | 1.5 | 1.5 | 1.5 | 1.5 | 1.5 | 1.5 | 1.5 |
| Cyclopentasiloxane | 34.5 | 34.5 | 34.5 | 34.5 | 34.5 | 36.0 | 35.5 |
| Titanium oxide, Al hydroxide, stearic acid #1 | 8.5 | 8.5 | 8.5 | 8.5 | 8.5 | 8.5 | 8.5 |
| Zinc oxide, hydrogen dimethicone #5 | 17.4 | 17.4 | 17.4 | 17.4 | 17.4 | 17.4 | 17.4 |
| Water | 20.3 | 20.3 | 20.3 | 20.3 | 20.3 | 20.3 | 20.3 |
| Propanediol | 6.0 | 6.0 | 6.0 | 6.0 | 6.0 | 6.0 | 6.0 |
| NaCl | 1.0 | 1.0 | 1.0 | 1.0 | 1.0 | 1.0 | 1.0 |
| Phenoxyethanol | 0.3 | 0.3 | 0.3 | 0.3 | 0.3 | 0.3 | 0.3 |
| SPF-Increasing Effect | 4 | 4 | 4 | 4 | 4 | 0 | |
| Usability (Smoothness) | 4 | 4 | 4 | 4 | 4 | 1 | 2 |
| Non-Powdery Finish | 4 | 4 | 4 | 4 | 4 | 1 | 1 |
| Stability of Formulation | 4 | 4 | 4 | 4 | 4 | 1 | 3 |
| Overall Rating | 16 | 16 | 16 | 16 | 16 | 3 | 7 |

| Display name | Example12 Comparative | Example13 \|Comparative\| | Example14 Comparative | Example15 Comparative | Example16 Comparative |
|---|---|---|---|---|---|
| Dextrin palmitate | — | — | — | — | — |
| Dextrin (palmitate/ethylhexanoate) | 0.5 | — | — | — | — |
| Inulin stearate | — | 0.5 | — | — | — |
| Dextrin myristate | — | — | 0.5 | — | — |
| Dextrin (palmitate/hexyldecanoate) | — | — | — | 0.5 | — |
| Dextrin isostearate | — | — | — | — | 1.0 |
| Squatane | 3.0 | 3.0 | 3.0 | 3.0 | 3.0 |
| Neopentylglycol dicaprate | 3.0 | 3.0 | 3.0 | 3.0 | 3.0 |
| Lauryl PEG-9 polydimethylsiloxyethyl dimethicone | 3.0 | 3.0 | 3.0 | 3.0 | 3.0 |
| Diphenylsiloxyphenyl | 1.5 | 1.5 | 1.5 | 1.5 | 1.5 |

TABLE 2-continued

| | | | | | |
|---|---|---|---|---|---|
| trimethicone | | | | | |
| Cyclopentasiloxane | 35.5 | 35.5 | 35.5 | 35.5 | 35.0 |
| Titanium oxide, Al hydroxide, stearic acid #1 | 8.5 | 8.5 | 8.5 | 8.5 | 8.5 |
| Zinc oxide, hydrogen dimethicone #5 | 17.4 | 17.4 | 17.4 | 17.4 | 17.4 |
| Water | 20.3 | 20.3 | 20.3 | 20.3 | 20.3 |
| Propanediol | 6.0 | 6.0 | 6.0 | 6.0 | 6.0 |
| NaCl | 1.0 | 1.0 | 1.0 | 1.0 | 1.0 |
| Phenoxyethanol | 0.3 | 0.3 | 0.3 | 0.3 | 0.3 |
| SPF-Increasing Effect | 1 | 1 | 1 | 1 | 2 |
| Usability (Smoothness) | 2 | 2 | 2 | 2 | 3 |
| Non-Powdery Finish | 1 | 1 | 1 | 1 | 4 |
| Stability of Formulation | 3 | 3 | 3 | 3 | 1 |
| Overall Rating | 7 | 7 | 7 | 7 | 10 |

TABLE 3

| Display name | Example20 | Example21 | Example22 | Example23 | Comparative Example17 |
|---|---|---|---|---|---|
| Dextrin palmitate | 1.0 | 1.0 | 1.0 | 1.0 | 1.0 |
| Dextrin isostearate | 2.0 | 2.0 | 2.0 | 2.0 | 2.0 |
| Titanium oxide, Al hydroxide, stearic acid #1 | 8.5 | — | — | 8.5 | — |
| Titanium oxide, Al hydroxide, stearic acid #2 | — | 8.5 | — | — | — |
| Titanium oxide, Al hydroxide, hydrogen dimethicone #3 | — | — | 8.5 | — | — |
| Titanium oxide, Al hydroxide, hydrogen dimethicone #4 | — | — | — | — | 8.5 |
| Zinc oxide, hydrogen dimethicone #5 | 17.4 | 17.4 | 17.4 | — | — |
| Zinc oxide, hydrogen dimethicone #6 | — | — | — | 17.4 | — |
| Zinc oxide, hydrogen dimethicone #7 | — | — | — | — | 17.4 |
| Squalane | 3.0 | 3.0 | 3.0 | 3.0 | 3.0 |
| Neopentylglycol dicaprate | 3.0 | 3.0 | 3.0 | 3.0 | 3.0 |
| Lauryl PEG-9 polydimethylsiloxyethyl dimethicone | 3.0 | 3.0 | 3.0 | 3.0 | 3.0 |
| Diphenylsiloxyphenyl trimethicone | 1.5 | 1.5 | 1.5 | 1.5 | 1.5 |
| Cyclopentasiloxane | 33.0 | 33.0 | 33.0 | 33.0 | 33.0 |
| Water | 20.3 | 20.3 | 20.3 | 20.3 | 20.3 |
| Propanediol | 6.0 | 6.0 | 6.0 | 6.0 | 6.0 |
| NaCl | 1.0 | 1.0 | 1.0 | 1.0 | 1.0 |
| Phenoxyethanol | 0.3 | 0.3 | 0.3 | 0.3 | 0.3 |
| SPF-Increasing Effect | 4 | 4 | 4 | 4 | 0 |
| Usability (Smoothness) | 4 | 4 | 4 | 4 | 1 |
| Non-Powdery Finish | 4 | 4 | 4 | 4 | 1 |
| Stability of Formulation | 4 | 4 | 4 | 4 | 1 |
| Overall Rating | 16 | 16 | 16 | 16 | 3 |

The above results indicate that a water-in-oil emulsion cosmetic comprising: a first polysaccharide fatty acid ester containing dextrin isostearate; a second polysaccharide fatty acid ester other than dextrin isostearate; and metal oxide particles; has improved ultraviolet-protective effect, excellent smoothness and non-powdery finish, and excellent dispersibility and emulsion stability.

Dextrin palmitate: Rheopearl KL2 (Chiba Flour Milling Co., Ltd.)

Dextrin isostearate: UNIFILMA HVY (Chiba Flour Milling Co., Ltd.)

Phytosqualane: Squalane (Sofim)

Neopentylglycol dicaprate: ESTEMOL N-01 (The Nisshin OilliO Group, Ltd.)

Lauryl PEG-9 polydimethylsiloxyethyl dimethicone: KF-6028 (Shin-Etsu Chemical Co., Ltd.)

Diphenylsiloxyphenyl trimethicone: KF-56A (Shin-Etsu Chemical Co., Ltd.)

Cyclopentasiloxane: KF-995 (Shin-Etsu Chemical Co., Ltd.) Titanium oxide, Al hydroxide, stearic acid #1: STV-455 (Titan Kogyo, Ltd.); average primary particle size, 60 nm Titanium oxide, Al hydroxide, stearic acid #2: ST-485SA15 (Titan Kogyo, Ltd.); average primary particle size, 54 nm Titanium oxide, Al hydroxide, hydrogen dimethicone #3: ST-457EC (Titan Kogyo, Ltd.); average primary particle size, 35 nm Titanium oxide, Al hydroxide, hydrogen dimethicone #4: Titanium DN-SH (2) (Dainihonkasei Co., Ltd.); average primary particle size, 250 nm Zinc oxide, hydrogen dimethicone #5: NANOFINE-50LP (Sakai Chemical Industry Co., Ltd.); average primary particle size, 20 nm Zinc oxide, hydrogen dimethicone #6: FINEX-30S-LPT (Sakai Chemical Industry Co., Ltd.); average primary particle size, 35 nm Zinc oxide, hydrogen dimethicone #7: XZ-1000F-LP (Sakai Chemical Industry Co., Ltd.); average primary particle size, 1000 nm Propanediol: Zemea Select Propanediol (Dupont Tate & Lyle Bio Products)

NaCl: Sodium chloride (Fukuda Seiyaku Co., Ltd.)

Phenoxyethanol: Phenoxyethanol S (Yokkaichi Chemical Co., Ltd.)

Dextrin (palmitate/ethylhexanoate): Rheopearl TT2 (Chiba Flour Milling Co., Ltd.)

Inulin stearate: Rheopearl ISK2 (Chiba Flour Milling Co., Ltd.)

Dextrin myristate: Rheopearl MKL2 (Chiba Flour Milling Co., Ltd.)

Dextrin (palmitate/hexyldecanoate): Rheopearl WX (Chiba Flour Milling Co., Ltd.)

The disclosure of Japanese Patent Application No. 2021-169526 (filing date: Oct. 15, 2021) is incorporated herein by reference in its entirety. All documents, patent applications, and technical standards cited in the present description are incorporated herein by reference to the same extent as in cases where the individual documents, patent applications, and technical standards are specifically and individually described to be incorporated by reference.

The invention claimed is:

1. A water-in-oil emulsion cosmetic comprising:

a first polysaccharide fatty acid ester containing dextrin isostearate;

a second polysaccharide fatty acid ester containing at least one selected from the group consisting of dextrin palmitate, dextrin (palmitate/ethylhexanoate), dextrin (palmitate/hexyldecanoate), inulin stearate, and dextrin myristate;

metal oxide particles having an average particle size of 5 nm to 80 nm; and water;

wherein a content ratio of the first polysaccharide fatty acid ester is 0.1% by mass to 4% by mass; and a content ratio of the second polysaccharide fatty acid ester is 0.1% by mass to 2% by mass;

a content ratio of the water is 15% by mass to 40% by mass;

the metal oxide particles contain at least zinc oxide and titanium oxide; and a content ratio of the metal oxide particles is 6% by mass to 40% by mass.

2. The water-in-oil emulsion cosmetic according to claim 1, wherein the total content ratio of the first polysaccharide fatty acid ester and the second polysaccharide fatty acid ester is 0.2% by mass to 4% by mass.

3. The water-in-oil emulsion cosmetic according to claim 1, wherein the mass ratio of the content of the second polysaccharide fatty acid ester to the content of the first polysaccharide fatty acid ester is 0.05 to 8.

4. The water-in-oil emulsion cosmetic according to claim 1, wherein the ratio of the content of the first polysaccharide fatty acid ester to the content of the metal oxide particles is 0.003 to 0.16.

5. The water-in-oil emulsion cosmetic according to claim 1, wherein the ratio of the content of the second polysaccharide fatty acid ester to the content of the metal oxide particles is 0.003 to 0.08.

6. The water-in-oil emulsion cosmetic according to claim 1, wherein the ratio of the total content of the first polysaccharide fatty acid ester and the second polysaccharide fatty acid ester to the total content of the metal oxide particles is 0.006 to 0.25.

7. The water-in-oil emulsion cosmetic according to claim 1, wherein the metal oxide particles have an average primary particle size of 10 nm to 50 nm.

8. The water-in-oil emulsion cosmetic according to claim 1, wherein a content ratio of the second polysaccharide fatty acid ester is 0.1% by mass to 2% by mass.

* * * * *